United States Patent [19]
Cox

[11] Patent Number: 5,249,455
[45] Date of Patent: Oct. 5, 1993

[54] B S & W MEASURING MEANS AND METHOD

[75] Inventor: Percy T. Cox, Houston, Tex.

[73] Assignee: Texaco Inc., White Plains, N.Y.

[21] Appl. No.: 811,633

[22] Filed: Dec. 23, 1991

[51] Int. Cl.$^5$ ............................................. G01N 27/22
[52] U.S. Cl. .................................. 73/61.44; 73/61.61; 324/689
[58] Field of Search ............ 324/689; 73/61.44, 61.61, 73/61.71

[56] References Cited

U.S. PATENT DOCUMENTS

| | | | |
|---|---|---|---|
| 2,720,624 | 10/1955 | Gunst et al. | 73/61.61 |
| 2,788,487 | 4/1957 | Grogg | 324/689 |
| 4,112,744 | 9/1978 | Tossano | 73/61.61 |
| 4,184,952 | 1/1980 | Stewart | 73/61.41 |
| 4,266,188 | 5/1981 | Thompson | 73/61.61 |
| 4,543,191 | 9/1985 | Stewart et al. | 324/689 |
| 4,849,687 | 7/1989 | Sims et al. | 73/61.41 |
| 4,854,725 | 8/1989 | Sims et al. | 73/61.41 |
| 5,033,289 | 7/1991 | Cox | 324/689 |

Primary Examiner—Hezron E. Williams
Assistant Examiner—George Dombroske
Attorney, Agent, or Firm—James J. O'Loughlin; Ronald G. Gillespie

[57] ABSTRACT

A water cut meter includes a test cell through which a petroleum stream will flow. The test cell includes an outer shell, a sensor probe which cooperates with the outer shell to form a sensor capacitor with the flow of the petroleum stream as the dielectric and a reference probe surrounded with pure oil as the dielectric to form a reference capacitor. Processing apparatus includes a comparator network electrically connected to the sensor capacitor and to reference capacitor which compares the capacitance of the sensor capacitor with the capacitance of the reference capacitor. The comparator network provides a signal corresponding to the capacitance difference between the sensor and reference capacitors. An output circuit connected to the comparator network provides an output corresponding to the water cut of the petroleum stream in accordance with the signal from the comparator network.

21 Claims, 4 Drawing Sheets

B S & W MEASURING MEANS AND METHOD

BACKGROUND OF THE INVENTION

1. Field of the Invention

The present invention relates to the water cut metering means and method in general, and more particularly, to a BS&W metering means and method.

SUMMARY OF THE INVENTION

A water cut meter includes a test cell through which a petroleum stream will flow. The test cell includes an outer shell, a sensor probe which cooperates with the outer shell to form a sensor capacitor with the flow of the petroleum stream as the dielectric and a reference probe surrounded with pure oil as the dielectric to form a reference capacitor. Processing apparatus includes a comparator network electrically connected to the sensor capacitor and to reference capacitor which compares the capacitance of the sensor capacitor with the capacitance of the reference capacitor. The comparator network provides a signal corresponding to the capacitance difference between the sensor and reference capacitors. An output circuit connected to the comparator network provides an output corresponding to the water cut of the petroleum stream in accordance with the signal from the comparator network.

The objects and advantages of the invention will appear more fully hereinafter from a consideration of the detailed description which follows, taken together with the accompanying drawings wherein two embodiments of the invention are illustrated by way of example. It is to be expressly understood, however, that the drawings are for illustration purposes only and are not to be construed as defining the limits of the invention.

DESCRIPTION OF THE INVENTION

Figure 1:
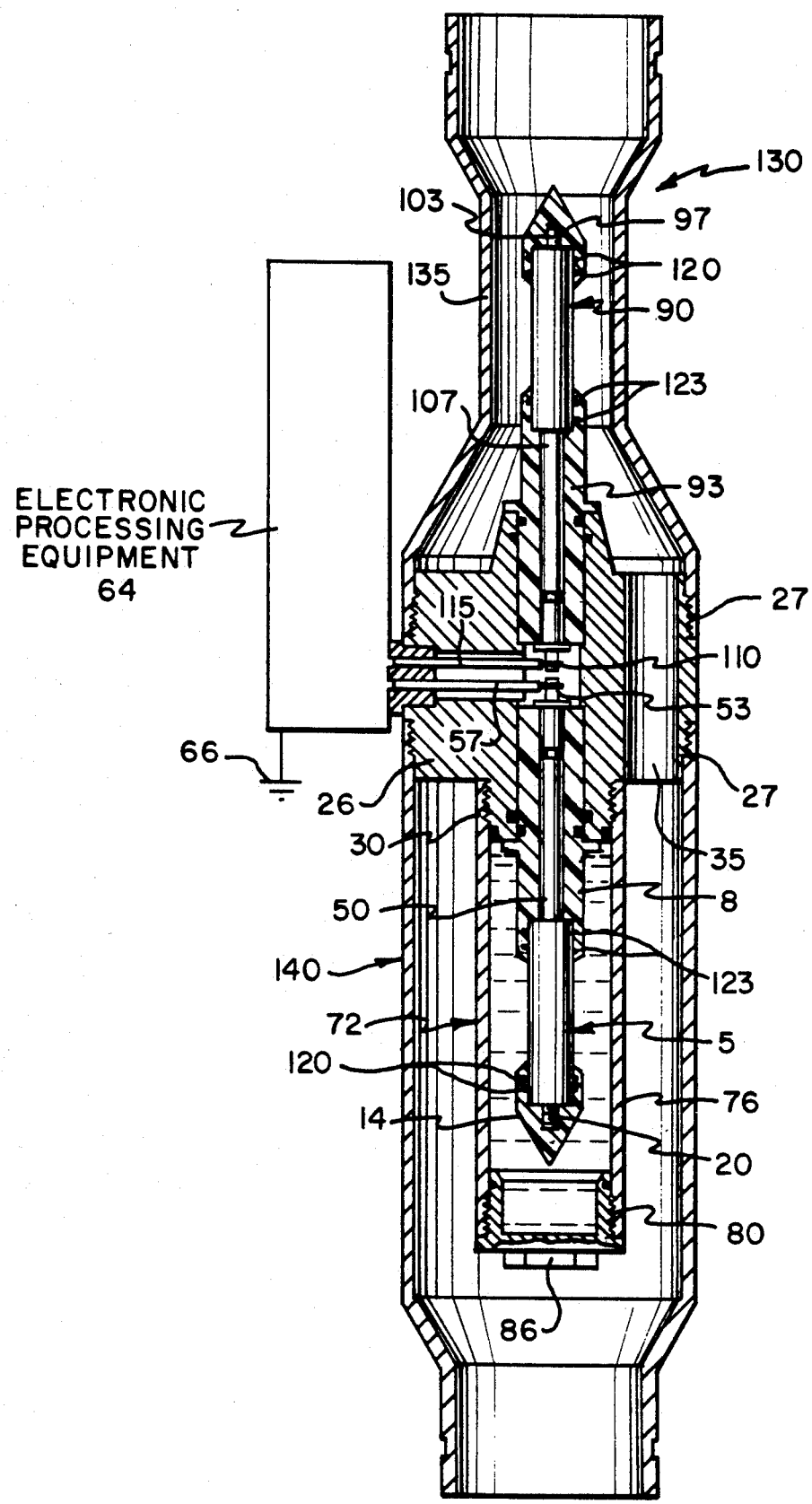
FIG. 1 is a drawing of a BS&W meter constructed in accordance with the present invention.

Referring to FIG. 1 there is shown a probe 5, which may be made of aluminum, held in position by a probe mount 8, which may be made of teflon or some other non conductive material. Attached to probe 5 is a probe tip 14, also made of teflon, and held in place by threads 20. A housing 26 has male threads 27 and 30 and a multiplicity of internal passageways 35 for permitting the flow of a petroleum stream. Probe 5 has a smaller diameter 50 which is connected to a right angle adapter 53. Adapter 53 is connected to another rod 57. Rod 57 is connected electrically to electronic processing equipment 64. Thus, there is an electrical conductive path from probe 5 to equipment 64. Probe 5 is covered with a thin heat shrinkable coating made of Kynar. Electronic processing equipment 64 is connected to ground 66.

A cylinder 72 having a body 76 is threaded onto housing 26. An end cap 80 is threaded to body 76. Dry oil of the type expected to be found in the petroleum stream is inserted through the opening in cylinder 72 and then sealed by end cap 80. Dry oil is defined as oil with no substantial water present. End cap 80 may also have a pressure equalization chamber so that no pressure difference exists across the cylinder wall.

A sensing probe 90, similar to probe 5, is held by a teflon probe mount 93. A probe tip 97 is attached to probe 90 by threads 103. The small diameter 107 of probe 90 connects to a right angle adapter 110. Right angle adapter 110 is connected to another rod 115 which is in turn is connected to electronic processing equipment 64.

Probe tips 14 and 97 are sealed with probes 5 and 90 respectively with O rings 120. Similarly probe 5 and 90 are sealed with probe mounts 8 and 93 respectfully with O rings 123. The large diameters of Probes 5 and 90 are covered with heat shrinkable coatings of Kynar.

Test cell 130 has a sleeve 135 connected to ground 66. It should be noted that sleeve 135 is sized at one end to a pipeline size and the other end to accommodate housing 26. In between sleeve 135 has a 2" inside diameter through a measurements section, that is the section in which probe 90 is located. Sleeve 135 is also manufactured to utilize a victaulic connection or, in the alternative, a flange may be attached to sleeve 135.

Sleeve 140 is threaded onto housing 26, and like sleeve 135 has adaption for victaulic connection or may also have a flange mounting attached to it. Thus, test cell 130 may be connected in line to a pipeline carrying the petroleum stream. The test cell may be mounted vertically so that gravity does not affect the flowing petroleum stream in a manner which would cause separation of oil and water. This promotes uniformity of the fluid by preventing fluid segregation.

Figure 2:
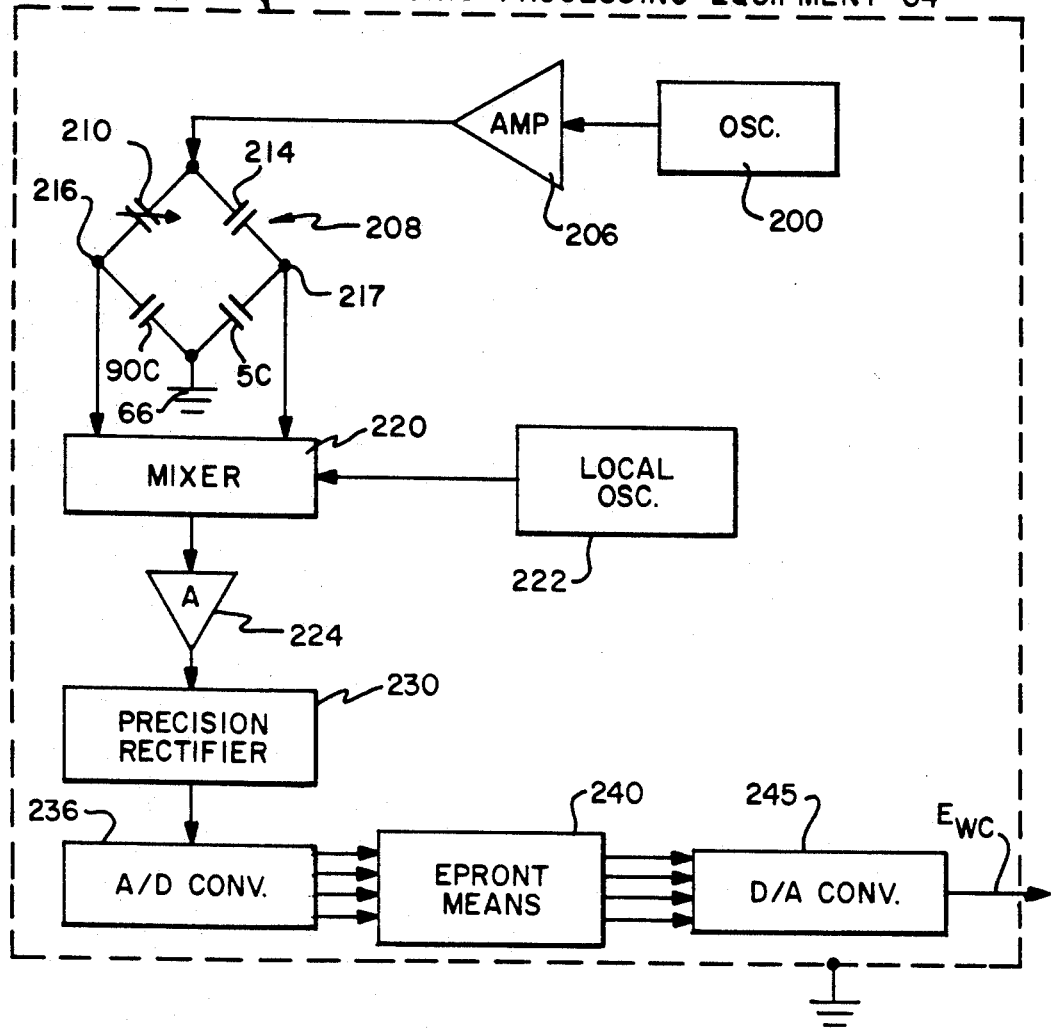
FIG. 2 is a detailed block diagram of one embodiment of the electronic processing equipment shown in FIG. 1.

With reference to FIG. 2, electronic processing equipment 64 includes a 20 MHz oscillator 200. Although a preferred frequency of 20 MHz is used, any frequency within a range of frequencies from 100 KHz to 200 MHz may be used. Oscillator 200 is connected to ground 66 as is all other units in electronic processing equipment 64 so that the signal path is with respect to ground 66. Oscillator 200 provides a signal to a driver/amplifier 206. The output of driver amplifier 206 is provided to a bridge circuit 208 comprising a variable capacitor 210, a fixed capacitor 214 and capacitors 90C and 5C which represent sensor probes 90 and 5 respectively. Outputs 216 and 217 of bridge circuit 208 are connected to a mixer 220. Any difference in capacitance between the measurement probe 90 and the reference probe 5 causes an unbalance in bridge 208 and generates an output signal, which is applied to mixer 220. This difference in capacitance is caused by water in the petroleum stream.

A local oscillator 222 provides a 19.998 MHz beat frequency signal to mixer 220, so that the signal from the output of bridge circuit 208 is hetrodyned to an intermediate frequency of 2 KHz. The output of mixer 220 is provided to an intermediate frequency amplifier 224. The signal from amplifier 224 is converted to a DC voltage $E_{out}$ by a precision rectifier 230.

The DC voltage from precision rectifier 230 is converted to digital signals by an A to D converter 236. The digital signals are provided to an EPROM means 240. EPROM means 240 is a programmable memory which converts the measured output voltage into a percent water cut using the previously stored data relating water cut to voltage ($E_{out}$). EPROM means 240 provides a digital output to a digital to analog converter 245, which in turns provides a 4-20 milliamp output as the water cut signal $E_{wc}$. It should be noted that the digital signals from EPROM means 240 may be used directly as a digital output of water cut.

Figure 3:
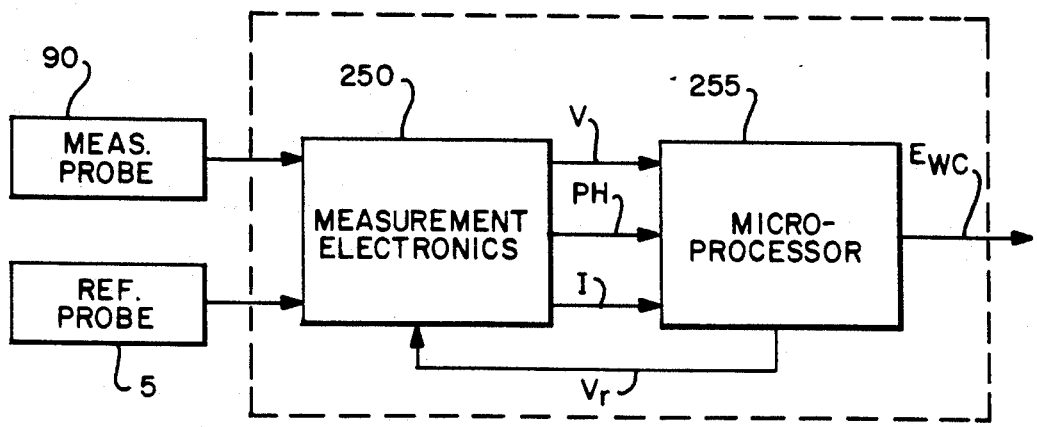
FIG. 3 is a detailed block diagram of a second embodiment of the electronic processing equipment shown in FIG. 1.

Referring now to FIG. 3, there is shown another embodiment of the present invention in which reference probe 5 and measurement probe 90 are connected to measurement electronics 250. Measurement electronics 250 provides a voltage signal V, a current signal I, and a phase signal PH to microprocessor means 255 which in turns provides a voltage $V_r$ to measurement electronics 250. Obviously, in order for the measurements to work, all of the units measurement electronics 250 and is measured with respect to ground 66 as well as microprocessor means 255.

Figure 4:
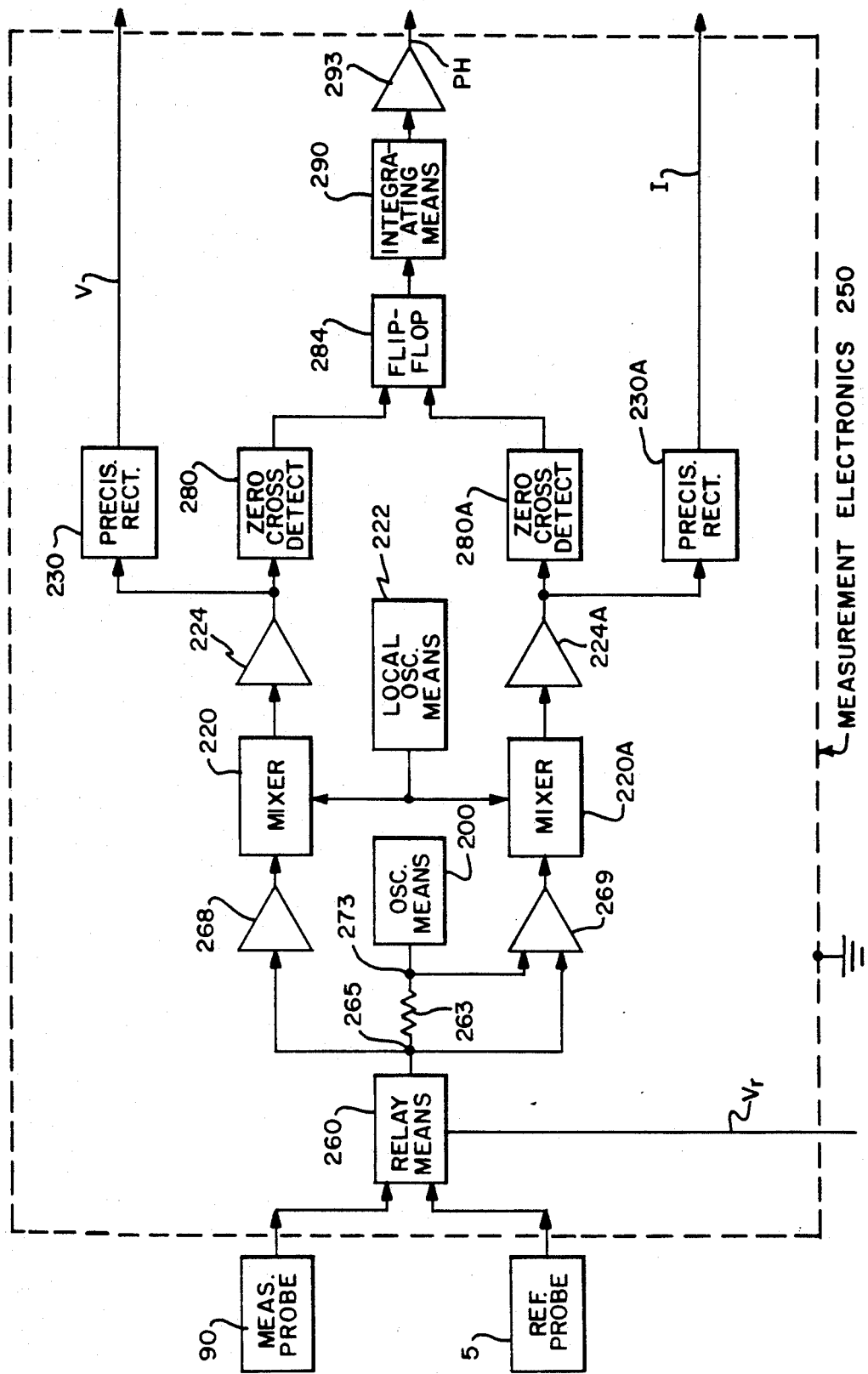
FIG. 4 is a detailed block diagram of the measurement electronics block shown in FIG. 3.

With reference to FIG. 4, relay means 260 is controlled by voltage $V_r$. It should be noted that elements having the same number as elements in FIG. 2 are the same elements. Further, that elements having the same numeric designation but with an alpha suffix operate in the same manner as elements having the same numeric designation without an alpha suffix. Relay means 260 is connected to a current measuring resistor 263 at a connection 265. Oscillator means 200 is connected to resistor 263 at a connection 273. A voltage appearing at connection 265 is provided to an amplifier 268 and to a difference amplifier 269. A voltage appearing at connection 273 is also provided to difference amplifier 269 whose output then corresponds to the current flowing through resistor 263.

The outputs from amplifiers 268 and 269 are provided to mixers 220 and 220A, which are receiving a signal from local oscillator means 222. The outputs from mixers 220 and 220A are provided through IF amplifiers 224 and 224A, respectively. The outputs from amplifiers 224 and 224A are provided to precision rectifiers 230 and 230A, respectively, which in turn rectifies them to provide the voltage signal V and the current signal I, respectively.

The outputs from amplifiers 224, 224A are also provided to zero crossing detectors 280 and 280A, respectively. Zero crossing detectors 280, 280A are responsive to the outputs from amplifiers 224 and 224A, respectively, to provide a rectangular voltage output to a flip-flop 284. Flip-flop 284, responsive to the signals from zero crossing detector 280 and 280A, provides a signal out which is related to the phase difference between the voltage signal V and the current signal I. The signal from flip-flop 284 is integrated by an integrating means 290 to provide a D.C. signal, corresponding to the phase difference, to a D.C. amplifier 293, where it is amplified and provided as signal PH.

Figure 5:
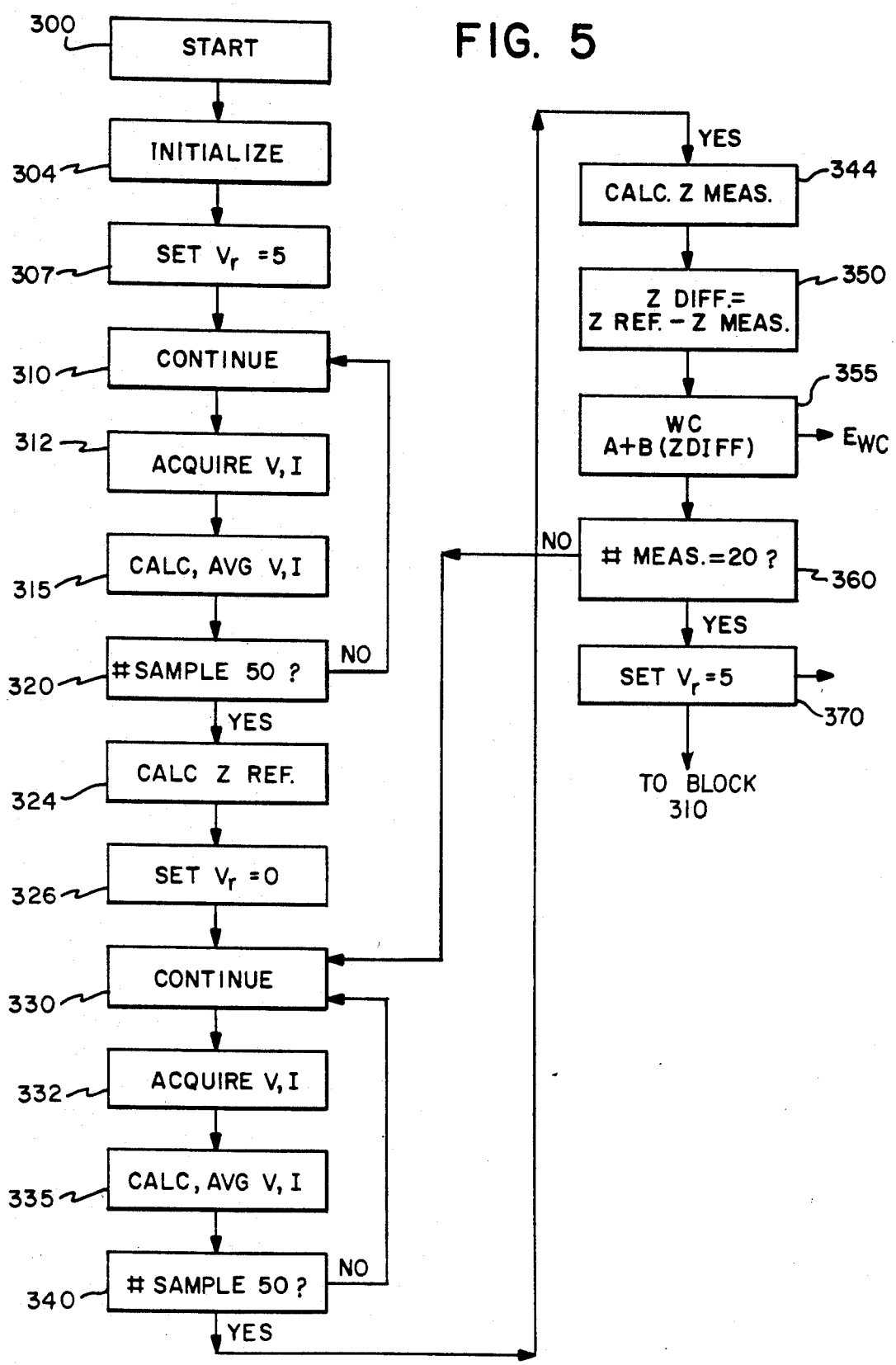
FIG. 5 is a flow diagram representing the operation of the second embodiment.

The sequence of operation can be seen in FIG. 5, where block 300 represents the starting of the process. The next step is in initialize the system which is represented by block 304, followed by the SET $V_r=5$ volts. The statement $V_r=5$ volts means that relay 260 connects the reference probe 5 to the other electronic elements in measuring electronics 250. The next block 310 is just a representation to continue with the voltage $V_r=5$, and we proceed to block 312 which is to acquire both signals V,I and as noted previously refers to the voltage and current measurements.

The next step, as represented by block 315, is to calculate the average V,I which is done by repetitively sampling V,I until the number of samples equals 50. This is indicated by block 320, "#SAMP=50?". If the answer to that question is "No", we go back to block 310 and continue until there are 50 samples. At that time, the answer to block 320 is "Yes", and we proceed to block 324 which is to calculate Z reference ($Z_{REF}$). Proceeding to the next block 326, "SET $V_r=0$". With $V_r$ at zero, relay means 260 connects measurement probe 90 to the electronic elements in measurements electronics 250.

Block 330 is similar to block 310, it indicates to continue. Again, we acquire V,I as proposed by block 332 and again, we proceed to blocks 335 which is to calculate the average of V,I and this again is accomplished through block 340 which asks the same question as block 320. Again, if the answer is that the number of samples does not equal 50, we return to block 330 to continue acquiring V,I until we have 50 samples. When the answer is "Yes", we proceed to block 344 "calculate Z measurement".

Block 350 requires the determination of Z difference ($Z_{DIFF}$) between Z reference and Z measurement. The water cut WC is then determined by block 355 where A and B are empirically derived constants. We then proceed to block 360 which asks the question, "#MEAS=2048". The answer is that we have not made 20 measurements and we return to the continue block 330. If the answer is "Yes", we proceed to block 370 SET $V_r=5$. The process then loops back to block 310 to continue measuring.

From the foregoing we can see that we sample V,I 50 times and use an average sample for the measurement probe and also for the reference probe. When we obtain the difference measurement, we repeat the measurements until we have 20 measurements. Then we start the process all over again by commanding relay 260 to disconnect the measurement probe 90 and to reconnect the reference probe 5.

As noted earlier, there is another signal that we have not discussed and that is signal PH. Signal PH relates to the phase difference between the voltage signal and the current signal. This signal is not necessary to the calculation of the water cut. However, as noted previously, the present invention is a BS&W meter which normally is used in oil continuous measurements, that is, the phase of the petroleum stream being monitored is oil continuous. However, if too much water occurs in the stream, so that the stream switches over to the water continuous phase, then the measurements would be invalid. Signal PH may be used and is used to notify the operator that there is too much water in the petroleum stream and that the measurements are therefore invalid measurements. It may be used in a number of ways which may include an alarm mechanism, a print out tied in with the print out of the water cuts to show that they are inaccurate, or it may even be used to blank out the water cut signal.

What is claimed is:

1. A BS&W meter comprising:
   test cell means for having a petroleum stream flowing through it including:
   an outer shell of conductive material,
   sensor probe means located within the outer shell for cooperating with the outer shell to form a sensor capacitor with the flowing petroleum stream as the dielectric, and
   a reference capacitor, located within the outer shell, which has pure oil as the dielectric; and processing means including:

comparator means electrically connected tot he sensor capacitor and to a reference probe means for comparing the capacitance of the sensor capacitor with the capacitance of the reference capacitor and providing a signal corresponding thereto, and output means connected to the comparator means for providing an output corresponding to the water cut of the petroleum stream in accordance with the signal from the comparator means, and in which the comparator means includes:

first oscillator means for providing a signal having a frequency within a desired range of frequencies, and capacitor means connected to the sensor capacitor and to the reference capacitor so as to form a bridge network for providing an output in accordance with the capacitance difference between the sensor capacitor and the reference capacitor, and in which the capacitor means includes:

a fixed capacitor connecting one of the capacitor in the test cell means to the first oscillator means, a variable capacitor connecting the other capacitor in the test cell means to the connection of the fixed capacitor and the first oscillator means, means connected to both capacitors in the test cell for providing a common ground connection for both capacitors in the test cell means, and conductive means connected to the connection of the fixed capacitor to a capacitor in the test cell means and to another connection of the variable capacitor to the other capacitor in the test cell means for providing the voltage across those two connections as the signal corresponding to the capacitance difference between the sensor capacitor and the reference capacitor.

2. A meter as described in claim 1 in which the output means include:

second oscillator means for providing a beat frequency signal, mixer means connected to the conductive means and to the second oscillator means responsive to the beat frequency signal to provide a signal at an intermediate frequency corresponding to the signal from the conductive means, rectifier means for rectifying the signal from the mixer means to provide a corresponding direct current signal, and utilizing means for utilizing the direct current signal from the rectifier means to provide the water cut signal.

3. A meter as described in claim 2 in which the utilizing means includes:

first converter means connected to the rectifier means for converting the direct current signal to digital signals, and memory means connected to the first converter means for using the digital signals to select a water cut value from stored values of water cuts for different combinations of oil and water in a petroleum stream and for providing digital signals, corresponding to the selected water cut, as the water cut output.

4. A meter as described in claim 1 and further comprising:

mounting means attached to the sensor probe means and to the reference probe means for mounting the sensor probe means and the reference probe means within the outer shell; and in which the reference capacitor includes:

housing means electrically connected to the outer shell for providing one electrode of the reference capacitor, the reference probe means for providing the other electrode of the reference capacitor, and wherein the pure oil is located within the housing so as to separate the two electrodes.

5. A meter as described in claim 4 in which the mounting means has a plurality of passageways for the petroleum stream to flow through it and additional passageways for electrical connection of the sensor probe means and the reference probe means to the comparator means.

6. A meter as described in claim 5 in which sensor probe means includes:

a first probe made of conductive material, a first probe tip made of non-conductive material attached to one end of the probe, and means made of non-conductive material and having a passageway therein for attaching the sensor probe means to the mounting means; and in which the outer shell is narrow in an area adjacent to the probe so that first probe and outer shell in that area form a co-axial capacitor.

7. A meter as described in claim 6 in which the reference probe means includes:

a second probe made of conductive material, a second probe tip made of non-conductive material attached to one end of the second probe, and means made of non-conductive material and having a passageway therein for attaching the sensor probe means to the mounting means, and means for encompassing the second probe in oil in a manner so as to cooperate with the second probe to form a capacitor with the oil as the dielectric.

8. A BS&W meter comprising:

test cell means for having a petroleum stream flowing through it including:

an outer shell of conductive material, sensor probe means located within the outer shell for cooperating with the outer shell to form a sensor capacitor with the flowing petroleum stream as the dielectric, and a reference capacitor, located within the outer shell, which has pure oil as the dielectric; and processing means including:

comparator means electrically connected to the sensor capacitor and to the reference probe means for comparing the capacitance of the sensor capacitor with the capacitance of the reference capacitor and providing a signal corresponding thereto, and output means connected to the comparator means for providing an output corresponding to the water cut of the petroleum stream in accordance with the signal from the comparator means; and in which the comparator means includes:

control means for providing a control signal, signal means for providing a voltage signal V and a current signal I in accordance with the capacitance of a capacitor, and switch means, responsive to the control signal, for connecting the sensor capacitor to the signal means while in a first state and connecting the reference capacitor to the signal means while in a second state so that the signals V and I are provided in accordance with the capacitance of the sensor capacitor or the reference capacitor.

9. A meter as described in claim 8 in which the signal means include:
   oscillator means for providing a driving signal at a preferred frequency within a range of frequencies,
   a current resistor connecting the oscillator means to the switching means,
   voltage means for utilizing a voltage at the connection of the current resistor had the switching means to provide a voltage output,
   signal V means connected to the voltage means for the voltage signal V in accordance with the voltage output,
   current means for utilizing the voltage across the current resistor to provide a current output, and
   signal I means for providing the current signal I in accordance with the current output.

10. A meter as described in claim 9 further comprising:
    means connected to the signal V means and to the signal I means for providing a signal PH corresponding to the phase difference between the voltage signal V and the current signal I.

11. A meter as described in claim 9 in which the output means includes:
    microprocessor means for providing the control signal to the switching means, and
    means for providing a water cut output in accordance with signals V and I.

12. A meter as described in claim 11 for determining the measured impedance $Z_{MEA}$ when the switching means is in the one state, and
    means for determining the reference impedance $Z_{REF}$ when the switching means is in the other state,
    means for determining the impedance difference $Z_{DIFF}$ in accordance with signal $Z_{REF}$ and $Z_{MEA}$, and providing a signal corresponding thereto, and
    means for determining the water cut in accordance with the following equation:

$$WC = A + B(Z_{DIFF}).$$

where A and B are empirically derived constants, and providing the output corresponding thereto.

13. A BS&W metering method comprising the steps of:
    causing a petroleum stream to flow through a test cell,
    using an outer shell of conductive material as part of the test cell,
    locating a sensor probe within the outer shell so that the sensor probe cooperates with the outer shell to form a sensor capacitor with the flowing petroleum stream as the dielectric, and
    locating a reference capacitor within the outer shell which has pure oil as the dielectric; and
    comparing the capacitance of the sensor capacitor with the capacitance of the reference capacitor,
    providing a comparison signal corresponding to the comparison, and
    providing an output corresponding to the watercut of the petroleum stream in accordance with the comparison signal; and
    providing a control signal,
    using signal means to provide a voltage signal V and a current signal I in accordance with the capacitance of a capacitor, and
    using switch means, responsive to the control signal, for connecting the sensor capacitor to the signal means while in a first state and connecting the reference capacitor to the signal means while in a second state so that the signals V and I are provided in accordance with the capacitance of the sensor capacitor or the reference capacitor.

14. A method as described in claim 13 in which the output step include:
    providing a beat frequency signal,
    mixer means mixing the comparison signal with the beat frequency signal to provide an intermediate frequency signal corresponding to the comparison signal,
    rectifying the intermediate frequency signal to provide a corresponding direct current signal, and
    utilizing the direct current signal to provide a water cut signal.

15. A as described in claim 14 in which the utilizing step includes:
    converting the direct current signal to digital signals,
    using the digital signals to select a water cut from memory means having stored values corresponding to water cuts for different combinations of water and oil in a petroleum stream, and
    providing digital signals, corresponding to the selected water cut value, as the water cut output.

16. A method as described in claim 13 which using the signal means step includes:
    providing a driving signal with an oscillator at a preferred frequency within a range of frequencies,
    connecting the oscillator to the switching means with a current resistor,
    utilizing a voltage at the connection of the current resistor and the switching means to provide a voltage output,
    providing the voltage signal V in accordance with the voltage output,
    utilizing the voltage across the current resistor to provide a current output, and
    providing the current signal I in accordance with the current output.

17. A method as described in claim 16 further comprising the step:
    providing a signal PH corresponding to the phase difference between the voltage signal V and the current signal I.

18. A method as describe in claim 13 in which the comparing step includes:
    providing a voltage signal $V_{MEA}$ functionally related to the capacitance of the sensor capacitor,
    providing a current signal $I_{MEA}$ functionally related to the capacitance of the sensor capacitor,
    providing a sensed impedance signal $Z_{MEA}$ in accordance with the voltage signal $V_{MEA}$ and the current signal $I_{MEA}$,
    providing a voltage signal $V_{REF}$ functionally related to the capacitance of the reference capacitor,
    providing a current signal $I_{REF}$ functionally related to the capacitance of the reference capacitor,
    providing a reference impedance signal $Z_{REF}$ in accordance with the voltage signal $V_{REF}$ and the current signal $I_{REF}$, and
    in which the comparison signal step includes:

providing a signal $Z_{DIFF}$, corresponding to the difference between the measured impedance $Z_{MEA}$ and the reference impedance $Z_{REF}$, as the comparison signal.

19. A method as described in claim 18 in which the steps of providing the voltage signal $V_{MEA}$, the current signal $I_{MEA}$, the voltage signal $V_{REF}$ and the current signal $I_{REF}$ are repeated 50 times, and further comprising the steps of:

averaging the voltage signals $V_{MEA}$, the current signals $I_{MEA}$, the voltage signals $V_{REF}$ and the current $I_{REF}$ to provide an average value voltage $\overline{V}_{MEA}$, an average current value $\overline{I}_{MEA}$, an average voltage signal $\overline{V}_{REF}$ and an average current signal $\overline{I}_{REF}$, respectively, providing the sensed impedance signal $Z_{MEA}$ in accordance with the average voltage signal $\overline{V}_{MEA}$, and the average current signal $\overline{I}_{MEA}$, and providing the signal $Z_{REF}$ in accordance with the average voltage signal $\overline{V}_{REF}$ and the average current signal $\overline{I}_{REF}$.

20. A method as described in claim 19 in which the output providing step includes:

determining the water cut of the petroleum stream in accordance with the following formula:

$$WC = A + B(Z_{DIFF})$$

where $A + B$ are empirically derived constants, and providing the output corresponding to the water cut as the determined water cut.

21. A method as described in claim 20 in which the water cut determining step is repeated 20 times.

* * * * *